United States Patent [19]

Woods et al.

[11] Patent Number: 5,099,011
[45] Date of Patent: Mar. 24, 1992

[54] **NUCLEIC ACID PROBE FOR DETECTION OF *NEISSERIA GONORRHOEA***

[75] Inventors: Derek Woods, Flemington; M. Jane Madonna, Middlesex, both of N.J.; Linda S. Mulcahy, Yardley, Pa.

[73] Assignee: Ortho Diagnostic Systems Inc., Raritan, N.J.

[21] Appl. No.: 703,361

[22] Filed: May 21, 1991

Related U.S. Application Data

[62] Division of Ser. No. 227,526, Aug. 2, 1988, Pat. No. 5,047,523.

[51] Int. Cl.$^5$ .............. C07H 15/12; C12Q 1/70; C12Q 1/68; C12N 11/02
[52] U.S. Cl. .............................. 536/27; 435/5; 435/6; 435/177; 435/822; 435/871
[58] Field of Search ............ 435/5, 6, 177, 822, 435/871; 536/27

[56] References Cited

U.S. PATENT DOCUMENTS

| | | | |
|---|---|---|---|
| 4,358,525 | 11/1982 | Falkow | 435/5 |
| 4,755,458 | 7/1988 | Rabbari | 435/5 |
| 4,794,082 | 12/1988 | Sigler | 435/177 |
| 5,047,523 | 9/1991 | Woods et al. | 536/27 |

FOREIGN PATENT DOCUMENTS

| | | |
|---|---|---|
| 0122614 | 10/1984 | European Pat. Off. . |
| 0123300 | 10/1984 | European Pat. Off. . |
| 0224126 | 11/1986 | European Pat. Off. . |
| 0237737 | 1/1987 | European Pat. Off. . |
| 0231495 | 8/1987 | European Pat. Off. . |
| 0301968 | 7/1988 | European Pat. Off. . |

OTHER PUBLICATIONS

Spratt et al., Gene, vol. 41, pp. 337-342 (1986).
"DNA Hybridization Techniques for the Detection of *Neisseria gonorrhoea* in Men with Urethritis", J. Infectious Diseases, vol. 48 (3): 462-471 (1983).
Maniatis et al., Molecular Cloning: A Laboratory Manual, 1982, Cold Spring Harbor Laboratory, p. 325.

*Primary Examiner*—Robert A. Wax
*Assistant Examiner*—Mindy B. Fleisher
*Attorney, Agent, or Firm*—Gale F. Matthews

[57] ABSTRACT

The invention discloses nucleic acid probes specific for *Neisseria gonorrhoea* useful in diagnostic methods to detect the presence of *N. gonorrhoea* in biological specimens.

12 Claims, No Drawings

NUCLEIC ACID PROBE FOR DETECTION OF *NEISSERIA GONORRHOEA*

This is a division of application Ser. No. 07/227,526, filed Aug. 2, 1988, now U.S. Pat. No. 5,047,523.

BACKGROUND OF THE INVENTION

*Neisseria gonorrhea* infection is one of the most prevalent sexually-transmitted bacterial diseases reported in humans. In response to this major health problem, numerous methods for detection of *Neisseria gonorrhoea* have been developed.

Most currently available procedures for the determination of gonococcal infection rely primarily upon culture techniques. Typical culture techniques include procedures described in Criteria and Techniques for the Diagnosis of Gonorrhea, published by the Center for Disease Control, Atlanta, Ga. In such culture techniques, a specimen, e.g., a urethral or cervical sample, is placed on an acceptable culture medium, e.g. Thayer-Martin medium. The cultures are incubated at 37° C. in a 5% carbon dioxide atmosphere for 24 to 48 hours. The culture plates are then inspected for the appearance of *Neisseria gonorrhoea* colonies. Suspect colonies are gram-stained and tested for oxidase activity. Generally, presumptive diagnosis of gonococcal infection in males is determined by obtaining urethral cultures which exhibit oxidase-positive colonies of gram-negative "coffee bean" shaped diplococci when cultured on Thayer-Martin medium. In females, gonococcal infection may be diagnosed by examining cervical cultures on Thayer-Martin medium wherein oxidase-positive colonies of gram-negative diplococci appear. Organisms from presumptively identified colonies of *Neisseria gonorrhoea* are frequently confirmed by sugar fermentation, fluorescent antibody staining or coagglutination. However, such culture procedures are laborious, time consuming and are generally limited to detection of living cells. When culture methods are utilized, a specimen may be taken at one location and shipped to a laboratory, usually at another location, where the organisms are cultured and identified. Thus, these culture procedures may require several days before results are obtained. Furthermore, results obtained from culture procedures may be erroneous, if rather exacting conditions for preservation, shipment and culturing of the bacteria are not followed.

The genetic information of all organisms is stored in specialized molecules called DNA. The unique structure of DNA was first described by Watson and Crick in 1953. The DNA molecule consists of two linear polymeric strands, intertwined to form a double helix. Each strand is composed of alternating sugar and phosphate groups, stabilized by hydrogen bonding between pairs of nucleotide bases: Adenine (A), guanine (G), cytosine (C), and thymine (T). The two strands are complementary, with A always bonding to T on the opposite strand and G always bonding to C. Thus, if the sequence of bases in one strand is known, the sequence of its partner is also known. The sugar and phosphate groups maintain the structural integrity of the DNA molecule and remain constant throughout the molecule. Only the number of base pairs and the sequence in which the base pairs occur will vary. It is the precise number and sequence of bases along the strand which encodes all genetic information. Hence, the physical and biological nature of all organisms is determined by the unique sequence of nucleotide bases in its DNA. The identity of an organism can be determined, and even minor differences between related organisms can be detected if the sequence of bases responsible is known and can be observed.

The double-stranded DNA molecule is normally very stable; however, the two complementary strands can be separated (denatured). In vivo, natural processes such as DNA replication (synthesis of identical "daughter" molecules) and transcription (synthesis of messenger RNA) require that the two strands separate and serve as templates. In vitro, DNA can be denatured by treatment with heat or extremes of pH. These simple procedures break the hydrogen bonds which hold the complementary pairs together while preserving the integrity of the base sequences in the relatively stable single-stranded DNA. Under appropriate conditions, because of the nucleotide complementarity and hydrogen bonding, the single strands will rewind (reanneal). This process in which a double-stranded molecule is formed by specific sequence-dependent interaction of complementary single strands is called nucleic acid hybridization.

Nucleic acid probes have been used a research tool for detecting sequences of DNA. These probes exploit the ability of complementary strands of nucleic acid to hybridize and form one strand of nucleic acid. Nucleic acid probes are specific nucleic acid sequences that search for complementary sequences in a pool of single-stranded nucleic acid. Under proper conditions, the complementary strands collide, complementary sequences recognize each other and reform double-stranded molecules. The nucleic acid probe can be labelled using either a radioisotope or one of several nonradioactive labels, thereby allowing visualization of the nucleic acid hybridization reaction.

A recently developed method of detecting gonococcal infection employs a polynucleotide probe to detect nucleic acid from the gonococcal cryptic plasmid. (See DNA Hybridization Technique for the Detection of *Neisseria gonorrhoea* in men with urethritis. *The Journal of Infectious Diseases*, vol. 148 (3): 462–471, (1983). A drawback to this method is the fact that not all of the known strains of *Neisseria gonorrhoea* contain this plasmid. Whether a particular strain contains the plasmid is dependant to some extent on the geographical area in which the strain is found. Thus, this method can only detect infection with strains having the plasmid and will not detect strains that do not contain the plasmid. The test will not be reliably accurate if used in areas where strains do not have the plasmid and will not detect the presence of infection in areas where the plasmid is present in the bacterium, but individuals have brought the infection to the area from one where the strain of gonorrhea does not have plasmids. To avoid these drawbacks, it would be useful to have methods of detecting *N. gonorrhoea* which use chromosomal DNA which will be present in all strains of the bacteria, rather than plasmid DNA which is present in only some strains.

More recently, a chromosomal DNA test has been disclosed in European patent application number 87101215.9, filing date 29.01.87, date of publication 23.09.87, claiming U.S. priority date 30.01.86. Nucleic acid probes disclosed in the application contain fragments of chromosomal DNA from *N. gonorrhoea*. It is reported that these can be used in nucleic acid hybridization methods to detect the presence of *N. gonorrhoea* in biological specimens. The fragments of chromosomal DNA used in the probes were characterized as being specific for *N. gonorrhoea* by comparative hybridization with chromosomal DNA from *N. meningitides*. *N. gonorrhoea* DNA fragments of up to about 1,300 base pairs which had a low percentage of hybridization with *N. meningitides* DNA were considered to be specific for *N. gonorrhoea* and useful for detecting the bacterium in diagnostic methods. Although this method may be sensitive to *N. gonorrhoea*, the long length of the nucleic acid fragments in the probes increases the likelihood that the sequences may be complementary to DNA sequences of other species and thus hybridize with them, producing false positive results in methods utilizing the probes. A DNA fragment containing fewer than about 12 nucleotides is believed to have insufficient complexity to be specific for a given organism; however, a much longer fragment has an increased likelihood of containing within it subsequences which are specific for another organism. To overcome this drawback of the longer probes, nucleic acid probes of shorter length are needed to detect the presence of *N. gonorrhoea* in biological specimens. Also, there is no suggestion whatsoever in this European patent application of the particular nucleic acid sequence of these fragments. Thus, these restriction fragment probes must be isolated from the chromosomal DNA and cannot be chemically synthesized de novo.

There is also a need for sensitive tests which have the ability to detect either broad or narrow groups of related species. The genus Neisseria includes two species that are pathogenic for humans, *N. gonorrhoea* and *N. meningitidis*. Although *N. gonorrhoea* is isolated from many patients with asymptomatic infections, it is always considered to be a pathogen. On the other hand, *N. meningitidis* may be isolated from the throat or nasopharynx in a small proportion of healthy individuals as well as patients with meningococcal disease. Other Neisseria species such as *N. sicca, N. lactamica* rarely cause disease but may be part of the normal flora and therefore must not be confused with gonococcus or meningococcus.

Accordingly, it is an object of the invention to provide means for accurate, rapid detection of *N. gonorrhoea* in biological specimens. It is a further object of the invention to provide nucleic acid probes for use in methods of detecting *N. gonorrhoea* in biological specimens which overcome the problems associated with nucleic acid probes available to date.

The advantages of the methods and probes as described herein are manifold. Nucleic acid hybridization methods which use the nucleic acid probes of the invention can be done on solid supports which require small quantities of reagents, and thus should be less expensive to perform than tests requiring larger amounts of reagents. Further advantages of this technology include the ability to detect the target organism regardless of its metabolic state, the ability to detect either broad or narrow groups of related species, and the potential for developing a single rapid procedure that uses the same basic format for all tests.

SUMMARY OF THE INVENTION

The invention provides nucleic acid probes useful for detecting *Neisseria gonorrhoea*, especially in diagnostic methods. The nucleic acid probes comprise a discrete nucleic acid sequence specific for *N. gonorrhoea* having about 20 to about 750 nucleotides, such probe being capable of binding to complementary target nucleic acid of *N. gonorrhoea* especially chromosomal nucleic acid. In preferred embodiments, the probe comprises about 30 to 600 nucleotides, more preferably about 30 to about 200 nucleotides. In the more preferred embodiments of the invention, the probe comprises all or a part of at least one nucleotide sequence selected from the group consisting of 5'...AGCTTTTTGGCGCTGCGTCCGGCTAACTGAT
ATCTGCATGGAGGCAACCGGCAGTTATTATGAAG
AAGTTGCCGCATACTTCGCGCAGTATTACAGCGT
TTACGTAGTGAACCCGCTGAAAATAAGCAAGTAT
GCAGAAAGCAGGTTCAAGCGAACCAAAACAGACA
AACAGGATGCAAAAGCTGATAGCGCTCAGTATTG
CCGGTCGCGGAAAGAAAGCGAGCTTGTAAAGAGG
CAGAAGCTACGGACACGAGCAATACAGGCTTTTA
CGGATGACGCCAGCTAACGCGTC...3', and 5'...ATTCCCGGGGATCGTAATCTCCGCTTTCTTA
TGTACGTGATACGCAATAACGGCGAGTTTACGCA
TCAATGCTGCGATGATGACTTTTTTAGGCTTCTT
CTTTTCTTCCAGTCTTGCTATGAAGTCGGGAAAT
GCCCTTATGCGGTATGCGACATGGCCGGCATAAA
CAAGACGGCGCGTAATTTCCTGTTGCCAAACTTG
GTCAGTTTGCCTTTTCCCCTTACGCTTGTCCCGG
ATTGACTTTTTGTTGCGGGCTTAAGCTGCGAACG
CTGCAAATTTGTTTGATGTTTCAAATTTCGAAGA
TGTTAGATGATGAAACACTAGCTGCGTCATTCTG
CTATGCGTATGTTCAGAGCTCAGCTCTGACGTAG
CTTCG...3'.

In particular, the nucleic acid probe may comprise all or a part of at least one discrete nucleotide sequence selected from the group consisting of 5' - AAA CGG AAC  GGC CAG TGC CAA
         GCT TTT TGG  CGC TGC GTC CGG
         CTA ACT GC- 3', 5' - ATA TCT GCA  TGG AGG CAA CCG
         GCA GTT ATT  ATG AAG AAG TTG
         CCG ACT AC- 3'

5'   GGA CGG CCA  GTG AAT TCC CGG
         GGA TCG TAA  TCT CCG CCT TTC
         TTA TGT A - 3',

5' - CGT GAT ACG  CAA TAA CGG CGA
         GTT TAC GCA  TCA ATG CTG CGA
         TGA TGA C - 3', and 5' - TTT TTA GGC  TTC TTC TTT TCT
         TCC AGT CTT  GCT ATG AAG TCG
         GGA AAT G - 3'.

In the particularly preferred embodiments of the invention, the probe comprises all or a part of at least one discrete nucleotide sequence selected from the group consisting of 5' - ATA TCT GCA  TGG AGG CAA CCG
         GCA GTT ATT  ATG AAG AAG TTG
         CCG ACT AC- 3' and

5' - CGT GAT ACG  CAA TAA CGG CGA
         GTT TAC GCA  TCA ATG CTG CGA
         TGA TGA C - 3'

The nucleotide sequences contained in the probes of the invention may be characterized as DNA or RNA. Similarly, the complementary nucleic acid of *N. gonorrhoea* which will be detected may be DNA or RNA. In preferred embodiments of the invention, the complementary nucleic acid of *N. gonorrhoea* which is detected is chromosomal DNA.

The nucleic acid probes of the invention may also comprise a subset, derivative, subclone or mutation of at least one of the discrete nucleotide sequences as described above. It should be appreciated, however, that the probes of the invention are capable of hybridizing to at least one insert obtained from deposited recombinant DNA having ATCC accession number 53409 and 53411 (American Type Culture Collection, Rockville, Md.). The nucleic acid probes may also comprise a nucleic acid sequence complementary to at least one of the discrete nucleic acid sequences as described above.

The nucleic acid probes of the invention may additionally comprise a 3' tail sequence having a detectable label bound thereon for signaling hybridization of the probe to a target sequence. In preferred embodiments, this is a 3' polynucleotide tail sequence having a detectable label bound thereon. In more preferred embodiments, the nucleotide sequence comprises adenosine and uridine.

The nucleic acid probes of the invention are preferably prepared by organic synthesis using methods known in the art.

The invention also provides reagents for use in detecting nucleic acid specific for *Neisseria gonorrhoea*. The reagents comprise at least one nucleic acid probe of the invention described herein specific for *Neisseria gonorrhoea* in a buffer solution. In the preferred reagents, there is also included a hybridization enhancer, a detergent and carrier DNA. The hybridization enhancer is preferably present in an amount of about 6% to 20% of total reagent volume. The reagents may also include a specificity enhancer. A preferred specificity enhancer is formamide.

DETAILED DESCRIPTION OF THE INVENTION

As used herein the term "specific to *Neisseria gonorrhoea*" refers to a nucleic acid sequence that is believed to be unique to *Neisseria gonorrhoea* and will hybridize by way of complementary base pair binding to a nucleic acid sequence from *Neisseria gonorrhoea* that contains at least some complementarity, termed a "target sequence". The sequences can be either RNA or DNA. It should be understood that this binding of the probe of the invention to the target sequence does not have to be perfectly matched. There may, in fact, be unpaired regions resulting in interior loops, bulge loops, hairpin loops, cruciform binding or any other mismatched regions. The key point is that hybridization must occur to the extent necessary to allow detection of the target sequence.

The length of the nucleic acid sequences in the probes of the invention is a length which is sufficient to allow hybridization to occur to at least a portion of the DNA of *Neisseria gonorrhoea*, especially chromosomal DNA, to allow detection of said DNA. Preferred for use herein, are probes having a nucleic acid sequence of about 20 to about 400 nucleotide bases long. It is more preferred that said sequences be about 20 to 200 bases long, most preferably about 20 to about 100 bases long.

In preferred embodiments, the probe comprises a nucleic acid sequence having at least about 20 nucleotide bases comprising in whole or in part at least one of the following sequences 5'...AGCTTTTTGGCGCTGCGTCCGGCTAACTGAT
ATCTGCATGGAGGCAACCGGCAGTTATTATGAAG
AAGTTGCCGCATACTTCGCGCAGTATTACAGCGT
TTACGTAGTGAACCCGCTGAAAATAAGCAAGTAT
GCAGAAAGCAGGTTCAAGCGAACCAAAACAGACA
AACAGGATGCAAAAGCTGATAGCGCTCAGTATTG
CCGGTCGCGGAAAGAAAGCGAGCTTGTAAAGAGG
CAGAAGCTACGGACACGAGCAATACAGGCTTTTA
CGGATGACGCCAGCTAACGCGTC...3', and 5'...ATTCCCGGGGATCGTAATCTCCGCTTTCTTA
TGTACGTGATACGCAATAACGGCGAGTTTACGCA
TCAATGCTGCGATGATGACTTTTTTAGGCTTCTT
CTTTTCTTCCAGTCTTGCTATGAAGTCGGGAAAT
GCCCTTATGCGGTATGCGACATGGCCGGCATAAA
CAAGACGGCGCGTAATTTCCTGTTGCCAAACTTG
GTCAGTTTGCCTTTTCCCCTTACGCTTGTCCCGG
ATTGACTTTTTGTTGCGGGCTTAAGCTGCGAACG
CTGCAAATTTGTTTGATGTTTCAAATTTCGAAGA
TGTTAGATGATGAAACACTAGCTGCGTCATTCTG
CTATGCGTATGTTCAGAGCTCAGCTCTGACGTAG
CTTCG...3'.

It should be appreciated that any part of the above sequence of at least about 20 nucleotide bases in length capable of hybridizing to the nucleic acid of *Neisseria gonorrhoea*, especially chromosomal DNA, is within the contemplation of the present invention. For example, a sequence of nucleic acid which begins in the middle of one of above-described sequences and extends further than the end of that sequence, and which detects *N. gonorrhoea* without appreciable cross-hybridization with other species is suitable for use in the invention. Overlapping sequences, combinations of smaller subsequences found within the sequences described above, and the like, are also included. Additional sequences that do not interfere with the hybridization abilities of the probe are also included, such as primer sequences, cloning site sequences, and any other type of flanking sequence.

More preferred embodiments of the nucleic acid probes comprise all or a portion of at least one of the following sequences:

```
5'- AAA CGG AAC   GGC CAG TGC CAA
    GCT TTT TGG   CGC TGC GTC CGG
    CTA ACT GC- 3',

5'- ATA TCT GCA   TGG AGG CAA CCG
    GCA GTT ATT   ATG AAG AAG TTG
    CCG ACT AC- 3'

5'  GGA CGG CCA   GTG AAT TCC CGG
    GGA TCG TAA   TCT CCG CCT TTC
    TTA TGT A - 3',

5'- CGT GAT ACG   CAA TAA CGG CGA
    GTT TAC GCA   TCA ATG CTG CGA
    TGA TGA C - 3',
``` and

```
5'- TTT TTA GGC   TTC TTC TTT TCT
    TCC AGT CTT   GCT ATG AAG TCG
    GGA AAT G - 3'.
```

In the most preferred embodiments, the nucleic acid probes comprise in whole or in part, at least one of the following sequences:

```
5'- ATA TCT GCA   TGG AGG CAA CCG
    GCA GTT ATT   ATG AAG AAG TTG
    CCG ACT AC- 3'
```

-continued and

5' - CGT GAT ACG  CAA TAA CGG CGA
    GTT TAC GCA   TCA ATG CTG CGA
    TGA TGA C - 3'

DNA sequences complementary to those specifically depicted above are also suitable for use in the invention. In vivo, DNA exists as double complementary strands. DNA hybridization method which utilize the probes of the invention break apart the double strands to provide single-stranded DNA which is then available to bind with the probe. The probes of the invention bind to one strand of the denatured double-stranded target DNA, whereas the complementary sequence of the probe would bind to the other strand.

Subsets, derivatives, subclones and mutations of the nucleotide sequences of the invention as detailed above, which do not detract from the ability of the nucleotide sequences to detect N. gonorrhoea, are also suitable for use in the invention. As used herein, the term "subsets" means nucleotide sequences having fewer than the entire number of nucleotides in a discrete nucleotide sequence. As used herein, the term "derivatives" means discrete nucleotide sequences of the invention having additional oligonucleotides not derived from N. gonorrhoea. These may be purposely attached, such as a polynucleotide sequence that may be termed a tail, or other sequences interspersed throughout the sequences taught herein which are not completely complementary to specific portions of the nucleic acid from N. gonorrhoea, but do not interfere with the overall ability of the probe to hybridize to the nucleic acid.

As used herein, the term "subclones" means fragments of the original nucleic acid sequences as taught herein, which have been inserted into a vector. It is well known in the art that subsets, derivatives, subclones and mutations of nucleotide sequences may function in the same way as the original nucleotide sequence.

The probes of the invention may be characterized in that they specifically bind to the nucleic acid of Neisseria gonorrhoeae, and in particular, to at least one discrete nucleic acid insert obtained from the genome of Neisseria gonorrhoeae, said inserts deposited in the form of recombinant DNA molecules with ATCC accession numbers 53409 and 53411 in the American Type Culture Collection, Rockville, Md., and having approximately 850 base pairs.

It should be appreciated that any such subclones, mutations, derivatives, fragments, and the like of the nucleic acid sequences taught hereunder may be easily tested for hybridization with these inserts. A Southern blot hybridization or similar test may be carried out to determine whether or not the attenuated sequences still retain the capability of binding to these inserts. European Patent Application 0 237 737 describes suitable techniques for obtaining an 850 base pair insert from these deposited recombinant DNA molecules, as well as hybridization procedures in general to determine whether or not a probe will hybridize to the insert.

The nucleic acid probes of the invention are labeled to signal hybridization to the target nucleic acid of Neisseria gonorrhea. The labeling may take on many forms, including conventional radioisotopic labeling, chemical labeling, immunogenic labeling, or a label with light scattering effect, and the like. Suitable methods to detect such labels are scintillation counting, autoradiography, fluorescence measurement, calorimetric measurement, or light emission measurement.

Thus, the labeling may comprise a radiolabel (e.g. $^{14}C$, $^{33}P$, $^{3}H$, and the like), an enzyme (e.g., peroxidase, alkaline or acid phosphatase, and the like), a bacterial label, a fluorescent label, an antibody (which may be used in a double antibody system), an antigen (to be used with a labeled antibody), a small molecule such as biotin (to be used with an avidin, streptavidin, or antobiotin system), a latex particle (to be used in a buoyancy or latex agglutination system), an electron dense compound such as ferritin (to be used with electron microscopy), or a light scattering particle such as colloidal gold, or any combinations or permutations of the foregoing.

For example, if the labeling portion of the probe is an antigen, a signal can be generated by complexing said antigen with an antibody/enzyme conjugate, followed by addition of an enzyme substrate. If this portion were an antibody, signal can be generated by complexing anti-antibody or an $F_C$ binding protein such as Protein A therewith, when such second antibody or Protein A have been conjugated to an enzyme.

For reasons of ease and safety in the handling of the probe, it is preferred that it be chemically labeled, especially enzymatically or immunologically. In more preferred embodiments, the chemical label of choice is a hapten such as biotin, iminobiotin, fluorescein and the like.

Among the preferred labeling systems that may be mentioned are those based on the biotin/strepavidin system. This system can be incorporated into the probe by a variety of means. For example, the probe can be covalently attached to biotin via a cytochrome c bridge (Manning et al, Biochemistry, 16: 1364–1370 (1977), Manning et al, Chromosoma, 53: 107–117 (1975)), Sodja, A., Nucleic Acids Research, 5: 385–401 (1978)), or the biotin can be covalently incorporated into specific nucleotide residues (Langer, P. R., Proceedings of one National Academy of Sciences, USA, 78: 6633–6637 (1981), or the biotin can be attached to a polynucleotide by means of a diamine (e.g., pentane diamine) bridge (Broker, T. R., et al, Nucleic Acids Research 5: 363–384 (1978)). Interaction of the biotin molecules with avidin, streptavidin or antibiotin antibodies is then carried out, wherein the avidin, streptavidin or the antibodies are conjugated to such signalling component as latex particles (Sodja, A., et al, supra, or Manning, et al Chromosma, supra.) ferritin (Broker, supra a fluorogen such as fluorescein, an enzyme, secondary antibodies, magnetic particles, or the like.

In the preferred embodiments, however, the chemical label is attached to a "tail sequence" which is affixed to the 3' terminal end of the probe. The tail sequence of the nucleic acid probes of the invention are preferably composed of nucleotide bases. In more preferred embodiments of the invention, the nucleotides are adenosine and uridine. In the most preferred embodiments of the invention the tail sequence has a composition of approximately 90% adenosine and 10% uridine. The nucleotide sequence of the tail is preferably approximately 200 to 400 bases long. The tail sequence is added to the probe by enzymatic reaction using terminal deoxynucleotidyl transferase (Pharmacia).

The nucleic acid sequences useful in the nucleic acid probes of the invention are readily prepared by any conventional method such as organic synthesis, recombinant DNA techniques or isolation from genomic DNA. However, these sequences are particularly amenable to organic synthesis using techniques known in the art, such as techniques utilizing a nucleic acid synthesizer and commercially available reagents.

Accordingly, then, the probes of the present invention are preferably made synthetically rather than being derived from genomic DNA or RNA. Methods of chemically synthesizing the oligonucleotide probes of the present invention are well known in the art. One such method is the phosphoramidite method described in Caruthers, et al. U.S. Pat. No. 4,458,066. Other methods are described in V. Amarnath et al. (1977), Chem Rev. 77: 183-217. Since the preferred probes of the present invention are relatively short, they therefore can be efficiently made by an automated DNA synthesizer. The probes may also conveniently be tailed with additional nucleotides, for example, biotin labeled nucleotides, preferably less than about 1000 bases, more preferably about 150 to about 500 bases, most preferably about 200-400 bases. Chemical synthesis of the probes makes it possible to easily produce large numbers of purified probes with specific nucleotide sequences rather than relying on the difficult recombinant procedures of isolating and purifying the genetic information from a natural source.

The probes may be provided in a lyophilized form, to be reconstituted in a buffer appropriate for conducting hybridization reactions. Alternatively, the probes may already be present in such a buffer or reagent solution, providing a reagent for detection of *N. gonorrhoea*. Such a reagent solution comprises agents that in general enhance the ability of the probe to bind to the target *Neisseria gonorrhea* DNA. For example, the reagent solution may contain any suitable hybridization enhancer, detergent, carrier DNA, and a compound to increase the specificity, such as formamide. Such a reagent solution may comprise one or more nucleotide sequences as described herein, in any combination, as the probe portion of the reagent. In the preferred embodiments, the reagent solution comprises formamide, specially in amounts of about 40% to about 60% of buffer volume, more preferably about 47% to about 55%. In the particularly preferred embodiments, the reagent solution also contains a hybridization enhancer in amounts ranging from about 6% to 40% of buffer volume, more particularly about 6% to about 16%, and most preferably about 10%.

The nucleic acid probes of the invention are particularly suited for detection of the nucleic acid of *N. gonorrhoea*, in samples suspected of containing same. One skilled in the art will appreciate that the nucleic acid from a microorganism to be identified is characteristic of the specific organism from which it is derived. Thus, detection of the specific nucleic acid sequence corresponds to detection of the organism in the sample tested. Accordingly, detection of nucleic acid characteristic of *N. gonorrhoea* in a biological specimen corresponds to detection of *N. gonorrhoea* in the specimen. Falkow U.S. Pat. No. 4,358,535 describes one general method of disease diagnosis involving labeled nucleotide probes complementary to a portion of the nucleic acid of a pathogen. This patent is herein incorporated by reference as it pertains to detection methodology.

However, the use of the probes as described herein is not limited to any specific means of hybridization of the probes to the target nucleic acid in a biological specimen, to detect the target sequence. Several hybridization assay techniques are known to the art and include, for example, dot blot hybridization, Southern blotting; sandwich hybridization assays such as those described by Ranki, et al., in U.S. Pat. Nos. 4,563,415 and 4,486,539; sandwich hybridization on beads as described by Hansen, et al. In European Patent Application No. 84306513.7; displacement hybridization techniques such as those described in WO 87/03911; capture techniques wherein the nucleic acid probes is first immobilized onto a solid support and then contacted with sample; in situ hybridization such as those cited or described by Ploeg, Folia Histochemica et Cytobiologica, Vol. 24 (1986) No. 3, pp 189-194; and the like.

EXAMPLES

The following examples more particularly describe certain aspects of the present invention but should not be considered limitative thereof.

EXAMPLE 1

Preparation of the Probes

Sequencing of a DNA Insert

A double-stranded DNA probe, derived from an MboI digest of *N. gonorrhoea*, also biotinylated, was received from Enzo Biochem, Inc., New York, N.Y. This nick translated, biotinylated probe had both a terminal Hind III and EcoRI endonuclease restriction enzyme site, resulting from subcloning experiments. Subsequently, sequence information was produced in order to chemically synthesize single-stranded probes. First, the nick translated probe was cloned into the Hind III-EcoRI cloning sites of a plasmid vector to replicate an amplified amount without the biotin label. This insert was then subcloned into the Hind III-EcoRI sites of the M13 phage sequencing vector. These samples of DNA were then sequenced using the method of Sanger et al., Proc. Natl. Acad. Sci., 74: 5463-5467, (1977).

Sequencing from the Hind III M13 vector cloning site produced the following sequence:

5'...AGCTTTTTGGCGCTGCGTCCGGCTAACTGAT
ATCTGCATGGAGGCAACCGGCAGTTATTA
TGAAGAAGTTGCCGACTACTTCGCGCAGT
ATTACAGCGTTTACGTAGTGAACCCGCTG
AAAATAAGCAAGTATGCAGAAAGCAGGTT
CAAGCGAACCAAAACAGACAAACAGGATG
CAAAAGCTGATAGCGCTCAGTATTGCCGG
TCGCGGAAAGAAAGCGAGCTTGTAAAGAG
GCAGAAGCTACGGACACGAGCAATACAGG
CTTTTACGGATGACGCCAGCTAACGCGTC
(AATCAAAGCGTAGCGCTGCATGAAACGT
CTACAGGCTAAGATAG)...3'.

Sequences in parentheses indicate an approximation, i.e.: this portion would be substantially as shown, but may differ by one or more bases.

Sequencing from the EcoRI M13 vector cloning site produced the following sequence:

5'...ATTCCCGGGGATCGTAATCTCCGCCTTTTCTTAT
GTACGTGATACGCAATAACGGCGAGTTTACGCATCA
ATGCTGCGATGATGACTTTTTTAGGCTTCTTCTTTTC
TTCCAGTCTTGCTATGAAGTCGGGAAATGCCCTTATG
CGGTATGCGACATGGCCGGCATAAACAAGACGGCGC
GTAATTTCCTGTTGCCAAACTTGGTCAGTTTGCCTTTT
CCCCTTACGCTTGTCCCGGATTGACTTTTTGTTGCGG
GCTTAAGCTGCGAACGCTGCAAATTTGTTTGATGTTT
CAAATTTCGAAGATGTTAGATGATGAAACACTAGCTG
CGTCATTCTGCTATGCG(G)TATGTTCAGAGCTCAGC

-continued
TCTGACGTAGCTTCG...3'

The (G) in the sequence above indicates that this base may or may not be present.

Starting at the 5' end, each fragment was arbitrarily divided into sequences of approximately 50 nucleotides and a corresponding synthetic oligonucleotide sequence for each of these units was synthesized. This was done for approximately the first 150 nucleotides of both sequences. The synthetic oligonucleotide were then tested for their ability to detect DNA of N. gonorrhoea.

The discrete nucleotide sequences below were synthesized for testing:

5'-AAA CGG AAC GGC CAG TGC CAA
GCT TTT TGG CGC TGC GTC CGG
CTA ACT GC-3'
(this sequence was designated CRL-10) (from the
5' end includes 19 nucleotide primer sequence and
6 nucleotide Hind III cloning site)

5'-ATA TCT GCA TGG AGG CAA CCG
GCA GTT ATT ATG AAG AAG TTG
CCG ACT AC-3'
(designated CRL-11)

5'-TTC GCG CAG TAT TAC AGC GTT
TAC GTA GTG AAC CCG CTG AAA
ATA AGC AA- 3'
(designated CRL-12) from the 5' end of the EcoRl fragment 5' GGA CGG CCA GTG AAT TCC CGG
GGA TCG TAA TCT CCG CCT TTC
TTA TGT A - 3'
(designated CRL-13) (from the 5' end includes 11
nucleotides from primer and 5 nucleotides from EcoRl
cloning site)

5'-CGT GAT ACG CAA TAA CGG CGA
GTT TAC GCA. TCA ATG CTG CGA
TGA TGA C -3'
(designated CRL-14)

5'-TTT TTA GGC TTC TTC TTT TCT
TCC AGT CTT GCT ATG AAG TCG
GGA AAT G -3'
(designated CRL-15)

EXAMPLE 2

Dot Blot Analysis of Binding of Synthetic Oligonucleotides to DNA of N. gonorrhoea 1. Synthetic oligonucleotide probes CRL-11, CRL-12, CRL-14 and CRL-15 were labeled with $^{32}P$ and used in dot blot hybridizations vs. purified chromosomal DNAs from one strain of N. gonorrhea, two strains of N. meningitidis, three strains of N. lactamica and one strain of E. coli.

CRL-11 and CRL-14 produced strong positive signals with N. gonorrhea and no non-specific signals with any other bacterial DNAs. CRL-12 produced a strong positive signal, but had some weak non-specific signals with one N. meningitidis and all three N. lactamica. CRL-15 produced a slightly weaker positive signal than the other oligonucleotides but had no non-specific signals.

2. CRL-11 was labeled with biotin and used in dot blot hybridizations v. purified chromosomal DNAs from 14 strains of N. gonorrhea, one strain of N. meningitidis and one strain of E. coli. All 14 N. gonorrhea strains were detected with this probe and there were no non-specific signals.

3. Seven synthetic oligonucleotides, CRL-11, CRL-12, CRL-14, CRL-15 were labeled with biotin and used in dot blot hybridizations vs. purified chromosomal DNAs from one strain of N. gonorrhea, two strains of N. meningitidis, three strains of N. lactamica and one strain of E. coli. Probes that produced strong positive signals and no non-specific signals include CRL-11 and CRL-14. Probes that produced weak positive signals and no non-specific signals include CRL-15. Finally, CRL-12 produced strong positive signal but also weak non-specific signals.

EXAMPLE 3

Assay Technique Using Nucleic Acid Probe

In the preferred embodiments in the detection of N. gonorrhoea from biological samples containing same, the microorganisms first are cultured. The N. gonorrhoea cultures may be grown on a selective enriched media such as straight, Thayer Martin (TM), modified Thayer Martin (MTM), New York City (NYC) or Martin Lewis to insure the isolation of pathogenic Neisseria species. Inoculated media are incubated at 35°-36° C. in a humid 3-7% carbon-dioxide atmosphere until bacterial growth is evident (16-24 hrs.). Cultures are then inspected visually for colony morphology. Isolates are not older than about 96 hours (4 days) before use in the methods of the invention.

The nucleic acid probe is labeled with biotin and the biotin is detected by binding streptavidin-horseradish peroxidase to the biotin and detecting the horseradish peroxidase with a chromogenic substrate. The hybridization reaction is preferably performed on a matrix such as Gene Screen Plus, nylon, cellulose, nitrocellulose or Biodyne. The matrix is generally known as a test dot. The matrix is preferably affixed to an inert surface having a flat surface such as a plastic paddle. Suspect organisms are lifted from the culture plates by gently touching the bacterial colony with the flattened end of an applicator stick. The applicator is then used to dab the bacteria onto the test dot. A single 1 mm colony is sufficient, so the test dot should not be overloaded. The bacteria should be applied as evenly as possible and damage to the test dot, by scratching tearing or excessive pressure, should be avoided. The inoculated test paddle is then placed on a heat block of 37° C. A small bead (approximately 10 microliters) of lysis reagent (0.5M alkali containing detergent) is added directly onto the test dot. The paddle is incubated for approximately one minute at 37° C. The paddle is then removed from the heat block and placed in a neutralizing reagent (0.5M Tris/HCl containing detergent) for one minute. The paddle is then returned directly to the heat block and without delay, excess reagent is blotted off with absorbent paper using firm direct pressure.

A small bead (approximately 10 microliters) of the probe reagent (biotinylated N. gonorrhoea specific probe and buffer containing 50% formamide, 10% hybridization enhancer, Triton X-100 and carrier DNA) is placed directly onto the test dot. The paddle is incubated for one minute at 37° C. and blotted as before. Then, a small bead (approximately 10 microliters) of conjugate reagent (streptavidin-horseradish peroxidase complex containing 1% carrier proteins and stabilizers and preservative, 0.02% thimerosal) is added directly onto the test dot and incubated for one minute at 37° C. The paddle is removed from the heat block and excess reagent is tapped off. The paddle is then placed in a wash reagent containing a reducing agent and detergent to wash off excess probe and enzyme conjugate. The paddle is soaked for two minutes and agitated intermittently. The paddle is returned to the heat block and blotted as before.

A small bead (approximately 10 microliters) of substrate solution (buffer containing hydrogen peroxide and tetramethylbenzidine (TMB; Biosynth International, Inc.) is added directly to the test dot. The paddle is incubated for one minute at 37° C. The paddle is removed from the heat block and placed in a stop reagent (1% sodium azide) for approximately 10 seconds. The paddle is then removed, blotted, and visually read to confirm the presence of $N$. gonorrhoea. A positive test for $N$. gonorrhoea produces a distinctive blue signal. The negative results range from no discernible signal to a faint blue background coloration.

Positive test samples are compared to positive and negative controls. Ideally, the positive control should be a fresh clinical isolate (less than 48 hrs. old) that has been definitively identified as $N$. gonorrhoea. Alternatively, a stock strain of $N$. gonorrhoea may be obtained from a recognized depository, such as the American Type Culture Collection (ATCC), Rockville, Md. 20850. Ideally, the negative control should be a fresh clinical isolate (less than 48 hrs. old) of a confirmed non-gonorrhea causing Neisseria species (e.g., $N$. meningitidis). Alternatively, a stock strain can be attained from the ATCC.

EXAMPLE 4

Performance Characteristics

The detection method described above, using the nucleic acid probes of the invention, was compared to the classic carbohydrate degradation test for identifying $N$. gonorrhoea and other Neisseria species.

The classic carbohydrate method used for identifying $N$. gonorrhoea and other Neisseria species can be found in Manual of Clinical Microbiology, 4th ed., E. Lennette, A. Balows, W. Hausler, H. Shadomy, 1985:181-2. The classic carbohydrate method used for identifying $N$. gonorrhoea and other Neisseria species is by determining their acid production from various carbohydrates in a Cystine Tryptic Agar (CTA) base medium. Conventional CTA media (GIBCO) which are semisolid agar deeps containing 1% filter-sterilized carbohydrate and a test battery generally including glucose, maltose, lactose, sucrose, fructose and a carbohydrate-free control tube were used for the assay.

Each subculture plate was examined to ascertain that the culture was pure. A gram stain and oxidase test were performed before the isolate was inoculated into the CTA sugars. Either of the following methods were used: (1) A dense suspension of the organisms in 0.5 ml sterile saline was prepared. With a capillary pipette, one drop of suspension was dispensed onto the surface of each agar deep, then the inoculum was stabbed into the upper third of the medium. (2) For each tube, a 3-mm loopful of growth was scraped from the surface of a chocolate agar plate and deposited a few millimeters below the surface of the medium. A change in the color of the phenol red indicator in the media from orange-pink to yellow signifies acid production from carbohydrate degradation.

Carbohydrate tubes were incubated at 35° C. to 37° C. in a standard, non-$CO_2$ incubator. Tubes were inspected at periodic intervals for 24 hours. Neisseriae gonorrhoea characteristically produces acid from glucose, but not from the other sugars.

| Sugar Fermentations Patterns of Neisseria sp. and B. Catarrhalis | | | | | |
|---|---|---|---|---|---|
| Organism | Glucose | Maltose | Lactose | Sucrose | Fructose |
| N. gonorrhoea | + | − | − | − | − |
| N. meningitidis | + | + | − | − | − |
| N. lactamica | + | + | − | + | + |
| N. sicca | + | + | − | + | + |
| N. subflava | + | + | − | V | V |
| N. mucosa | + | + | − | + | + |
| N. flavescens | − | − | − | − | − |
| N. cinerea | − | − | − | − | − |
| N. elongata | − | − | − | − | − |
| B. catarrhalis | − | − | − | − | − |

A total of 361 genital and pharyngeal isolates were tested (Table I). The detection method and probes of the invention detected 174/174 confirmed gonococcus (GC) and gave negative results for 157/158 non-GC isolates. One (1) $N$. meningitidis[30] reacted weakly upon initial testing but repeat testing yielded consistently negative results (Table II). Overall agreement between the presently claimed probes and methods and the reference method is 99.7%.

TABLE I

| Organism | Isolates Tested |
|---|---|
| N. gonorrhoea | 174 |
| N. meningitidis | 158 |
| N. lactamica | 10 |
| N. cinerea | 6 |
| Other Neisseria | 13 |
| Total | 361 |

TABLE II

| Organism | Carbohydrate Degradation | Hybridization Test Positive | Hybridization Test Negative |
|---|---|---|---|
| N. gonorrhoea | 174 | 174 | 0 |
| N. meningitidis | 158 | 1+ | 157 |
| Other Neisseria | 29 | 0 | 29 |
| Sensitivity | | 174/174 = 100% | |
| Specificity | | 157/158 = 99.4% | |
| Agreement | | 360/361 = 99.7% | |

In addition, 38 strains of non-Neisseria species were tested and gave negative results with the probes of the invention and claimed detection method (Table III).

TABLE III

| Neisseria Species | Test Result |
|---|---|
| N. gonorrhoea* | + |
| Auxotype 16 (AAU) | |
| Auxotype 12 | |
| Auxotype 22 | |
| Auxotype 9 | |
| Auxotype 5 | |
| Auxotype 1 | |
| N. meningitidis | − |
| N. lactamica | − |
| N. subflava | − |
| N. cinerea | − |
| N. sicca | − |
| N. elongata | − |
| N. polysaccharae | − |
| N. mucosa | − |
| Kingella dentrificans | − |
| Staphylococcus sp | − |
| Streptococcus sp | − |
| Lactobacillus | − |
| Diptheroids | − |
| Candida albicans | − |
| Enterobacter cloacae | − |

TABLE III-continued

| Neisseria Species | Test Result |
|---|---|
| Klebsiella pneumoniae | − |
| Branhamella catarrhalis | − |
| Escherichia coli | − |
| Aeromonas hydrophila | − |
| Morganella morganii | − |
| Serratia sp | − |
| Citrobacter freundii | − |
| Shigella sp | − |
| Salmonella sp | − |
| Hemophilus | − |
| Flavobacterium meningosepticum | − |
| Moraxella sp | − |
| Bordetella bronchiseptica | − |
| Gardnerella vaginalis | − |
| Yersinia enterocolitica | − |
| Proteus sp | − |
| Flavobacterium meningosepticum | − |
| Micrococcus luteus | − |
| Bacillus sp | − |

*Representative strains from all 9 Principle Outer Membrane Protein (POMP) serotypes were tested with the probe and were reactive.

What is claimed is:

1. A reagent for use in detecting nucleic acid specific for *Neisseria gonorrhoea*, comprising,
    at least one nucleic acid probe consisting essentially of at least one nucleotide sequence having a length of from 30 to 600 bases selected from the group consisting of 5'... AGCTTTTTGGCGCTGCGTCCGGCTAACTGATAT
CTGCATGGAGGCAACCGGCAGTTATTATGAAGAA
GTTGCCGACTACTTCGCGCAGTATTACAGCGTTT
ACGTAGTGAACCCGCTGAAAATAAGCAAGTATGC
AGAAAGCAGGTTCAAGCGAACCAAAACAGACAAA
CAGGATGCAAAAGCTGATAGCGCTCAGTATTGCC
GGTCGCGGAAAGAAAGCGAGCTTGTAAAGAGGCA
GAAGCTACGGACACGAGCAATACAGGCTTTTACG
GATGACGCCAGCTAACGCGTCAATCAAAGCGTAG
CGCTGCATGAAACGTCTACAGGC
TAAGATAG... 3' and

5'... ATTCCCGGGGATCGTAATCTCCGCCTTTCTTAT
GTACGTGATACGCAATAACGGCGAGTTTACGCAT
CAATGCTGCGATGATGACTTTTTTAGGCTTCTTC
TTTTCTTCCAGTCTTGCTATGAAGTCGGGAAATG
CCCTTATGCGGTATGCGACATGGCCGGCATAAAC
AAGACGGCGCGTAATTTCCTGTTGCCAAACTTGG
TCAGTTTGCCTTTTCCCCTTACGCTTGTCCCGGA
TTGACTTTTTGTTGCGGGCTTAAGCTGCGAACGC
TGCAAATTTGTTTGATGTTTCAAATTTCGAAGATG
TTAGATGATGAAACACTAGCTGCGTCATTCTGCT
ATGCGGTATGTTCAGAGCTCAGCTCTGACGTAGC
TTCG... 3', said probe dispersed in a buffer solution.

2. The reagent of claim 1 further comprising
    a hybridization enhancer;
    a detergent; and
    carrier DNA.

3. The reagent of claim 2 wherein said hybridization enhancer is present in an amount of about 6% to 20% of total reagent volume.

4. The reagent of claim 2 further comprising a specificity enhancer.

5. The reagent of claim 4 wherein said specificity enhancer is formamide.

6. The reagent of claim 3 further comprising a specificity enhancer.

7. The reagent of claim 6 wherein said specificity enhancer is formamide.

8. The reagent of claim 1 wherein said nucleic acid probe further comprises a tail sequence having a detectable label bound thereon.

9. The reagent of claim 8 wherein said tail sequence comprises a nucleotide sequence.

10. The reagent of claim 9 wherein said nucleotide sequence comprises adenine and uridine.

11. The reagent of claim 10 wherein said uridine has a detectable label bound thereon.

12. The reagent of claim 11 wherein said detectable label is biotin.

* * * * *